US006232276B1

(12) United States Patent
Stiefel et al.

(10) Patent No.: US 6,232,276 B1
(45) Date of Patent: *May 15, 2001

(54) TRINUCLEAR MOLYBDENUM MULTIFUNCTIONAL ADDITIVE FOR LUBRICATING OILS

(75) Inventors: Edward Ira Stiefel, Bridgewater; Jonathan M. McConnachie; Daniel Paul Leta, both of Flemington; Manuel A. Francisco, Washington; Catherine Louise Coyle, Mendham, all of NJ (US); Peter John Guzi, Baton Rouge, LA (US); Charles F. Pictroski, Glen Gardner, NJ (US)

(73) Assignee: Infineum USA L.P., Linden, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/844,019

(22) Filed: Apr. 18, 1997

Related U.S. Application Data

(63) Continuation-in-part of application No. 08/766,831, filed on Dec. 13, 1996, now abandoned.

(51) Int. Cl.$^7$ ................................................. C10M 139/00
(52) U.S. Cl. ........................ 508/363; 508/364; 508/370; 508/379; 508/445; 556/38; 556/57
(58) Field of Search .................................... 508/363, 364, 508/370, 379, 445; 556/38, 57

(56) References Cited

U.S. PATENT DOCUMENTS

| | | | |
|---|---|---|---|
| 3,400,140 | 9/1968 | Rowan et al. | 260/429 |
| 4,559,152 | * 12/1985 | Schlicht | 252/32.7 E |
| 4,789,492 | 12/1988 | Katsumata et al. | 252/32.7 E |
| 4,846,983 | * 7/1989 | Ward, Jr. | 252/33.6 |
| 4,966,719 | 10/1990 | Coyle et al. | |
| 4,978,464 | 12/1990 | Coyle et al. | |
| 4,995,996 | 2/1991 | Coyle et al. | |
| 5,824,627 | * 10/1998 | McConnachie et al. | 508/363 |
| 5,837,657 | * 11/1998 | Faug et al. | 508/363 |
| 5,888,945 | * 3/1999 | Stiefel et al. | 508/363 |
| 5,906,968 | * 5/1999 | McConnachie et al. | 508/363 |
| 6,010,987 | * 1/2000 | Stiefel et al. | 508/363 |

OTHER PUBLICATIONS

Proceedings of the 4th Climax International Conference on Chemistry and Uses of Molybdenum, Climax Molybenum, Ann Arbor, MI 1982, pp. 212–217.
Proceedings of the 4th Climax International Conference on Chemistry and Uses of Molybdenum, Climax Molybdenum, Ann Arbor, MI 1982, pp. 98–101.
Review by Shibahara in Coordination Chemistry Reviews, 1993, vol. 123, pp. 73–147.
Shibahara, et al.; Coord. Chem. Rev. 123, 73–148 (1993).
Doner, et al.; International Publication WO95/19411, Pub. Jul. 20, 1995 for Int'l. Appl. No. PCT/US95/00242.
Meienberger et al., "The reactivity of complexes containing the . . . ", Inorganica Chimica Acta. 213 (1993) pp. 157–169.*

* cited by examiner

Primary Examiner—Jerry D. Johnson

(57) ABSTRACT

A lubricating oil composition is provided comprising a major amount of an oil of lubricating viscosity and a minor amount of at least one trinuclear molybdenum compound. Preferably, the trinuclear molybdenum compound is selected from those compounds having the formula $Mo_3S_kL_4Q_z$ and mixtures thereof in which L is a ligand having organo groups with a sufficient number of carbon atoms to render the compound soluble in the oil, k varies from 4 through 7, Q is selected from the group of compounds having lone pair electrons including water, amines, alcohols, phosphines, and ethers, and z ranges from 0 to 5. In general, the organo groups of the mono-anionic ligands will be the same although they may be different, and they preferably are selected from alkyl, aryl, substituted aryl, and ether groups. For example, when L is a dialkyldithiocarbamate or a dialkyldithiophosphate, the alkyl groups will have from about 1 to 30 carbon atoms.

31 Claims, No Drawings

TRINUCLEAR MOLYBDENUM MULTIFUNCTIONAL ADDITIVE FOR LUBRICATING OILS

This Application is a Continuation-in-Part of U.S. patent application Ser. No. 08/766,831 filed Dec. 13, 1996 now abandoned.

FIELD OF THE INVENTION

The present invention relates to improved lubricating compositions. The present invention also relates to lubricant compositions containing trinuclear molybdenum compounds.

BACKGROUND OF THE INVENTION

Molybdenum disulfide is a known lubricant additive. Unfortunately, it has certain known disadvantages some of which are caused by its insolubility in lubricating oils. Therefore, oil-soluble molybdenum sulfide-containing compounds have been proposed and investigated as lubricant additives. For example, U.S. Pat. No. 2,951,040 discloses an oil-soluble molybdic xanthate as useful in lubricating compositions.

U.S. Pat. No. 3,419,589 discloses the use of certain "sulfurized" molybdenum (VI) dithiocarbamates as lubricant additives. These additives are described as being oil-soluble or at least capable of being easily suspended in oils.

U.S. Pat. No. 3,840,463 discloses the use of certain metal dithiocarbamates or dithiophosphates in combination with metal-free additives that contain sulfur and phosphorus.

U.S. Pat. No. 4,966,719, U.S. Pat. No. 4,995,996, and U.S. Pat. No. 4,978,464 all relate to the preparation and use of molybdenum-sulfur compounds. However, the materials described in those patents are prepared from starting materials that are themselves either relatively expensive or difficult to prepare.

The foregoing patents are listed as representative of the very many known lubricant additives containing both molybdenum and sulfur.

As is known in the art, some lubricant additives function as antiwear agents, some as antioxidants, some as friction modifiers, and some as extreme pressure agents. Indeed, some additives may satisfy more than one of these functions. For example, metal dithiophosphates represent a class of additives which are known to exhibit antioxidant and antiwear properties. The most commonly used additives in this class are the zinc dialkyldithiophosphates (ZDDP) which provide excellent oxidation resistance and exhibit superior antiwear properties. Unfortunately, they do not have the most desirable lubricity. Therefore, lubricating compositions containing these zinc compounds may also require inclusion of friction modifiers, which may lead to other problems, such as additive compatibility, in formulating effective lubricant compositions. Additives may lose their effectiveness when combined with incompatible additives in a lubricating composition. Generally, extreme care must be exercised in combining various additives to assure both compatibility and effectiveness. For example, some friction modifiers affect metal surfaces differently than antiwear agents do. When both are present, friction-reducing and antiwear additives may compete for the surface of the metal parts which are subject to lubrication. This competition can produce a lubricant that is less effective than is suggested by the individual properties of the additive components.

Trinuclear molybdenum compounds have been reported, but they are either ionic or have ligands with short chain alkyl groups. The reported compounds are consequently not oil soluble, and they have not been reported as lubricating oil additives.

Thus, there remains a need for improved lubricating oil additives that can be used with standard lubricating oils, are compatible with other conventional lubricant additives, and can be made from readily available starting materials.

SUMMARY OF THE INVENTION

The invention is a lubricating composition comprising a major amount of an oil of lubricating viscosity and a minor amount of at least one trinuclear molybdenum compound. Preferably, the trinuclear molybdenum compound has a sulfur containing core and is represented by the formula $Mo_3S_kL_nQ_z$, wherein L represents independently selected ligands, n varies from 1 to 4 and is preferably 4, k varies from 4 through 7 and is preferably 4 or 7, Q is selected from the group consisting of neutral electron donating compounds including water, amines, alcohols, phosphines, and ethers, and z ranges from 0 to 5.

In another embodiment, the invention relates to mixtures of such compounds.

The lubricant compositions according to this invention have excellent antiwear, antioxidant, and friction-reducing properties. The lubricant compositions of the present invention may also be compatible with other standard additives used in formulating commercial lubricating compositions and can be made from readily available starting materials.

In still another embodiment, the invention relates to a composition having the formula $Mo_3S_kL_nQ_z$, wherein L represents independently selected ligands, n varies from 1 to 4, k varies from 4 through 7, Q is selected from the group consisting of neutral electron donating compounds including water, amines, alcohols, phosphines, and ethers, and z ranges from 0 to 5.

DETAILED DESCRIPTION OF THE INVENTION

The lubricant compositions of the present invention include a major amount of oil of lubricating viscosity. This oil may be selected from vegetable, animal, mineral, or synthetic oils. The oils may range in viscosity from light distillate mineral oils to heavy lubricating oils such as gas engine oil, mineral lubricating oil, motor vehicle oil, and heavy duty diesel oil. The oils may be unrefined, refined, and re-refined.

In general, the viscosity of the oil will range from about 2 centistokes to about 30 centistokes and especially in the range of 5 centistokes to 20 centistokes at 100° C.

The lubricant compositions of the present invention include a minor amount of a compound selected from compounds having the formula $Mo_3S_kL_nQ_z$ and mixtures thereof wherein the L are independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms should be present among all the ligands' organo groups, such as at least 25, at least 30, or at least 35 carbon atoms.

The ligands are independently selected from the group of

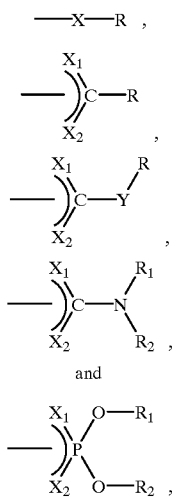

and mixtures thereof, wherein X, $X_1$, $X_2$, and Y are independently selected from the group of oxygen and sulfur, and wherein $R_1$, $R_2$, and R are independently selected from hydrogen and organo groups that may be the same or different. Preferably the organo groups are hydrocarbyl groups such as alkyl (e.g., in which the carbon atom attached to the remainder of the ligand is primary or secondary), aryl, substituted aryl and ether groups. More preferably, each ligand has the same hydrocarbyl group.

The term "hydrocarbyl" denotes a substituent having carbon atoms directly attached to the remainder of the ligand and is predominantly hydrocarbyl in character within the context of this invention. Such substituents include the following:

1. Hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei and the like, as well as cyclic substituents wherein the ring is completed through another portion of the ligand (that is, any two indicated substituents may together form an alicyclic group).
2. Substituted hydrocarbon substituents, that is, those containing non-hydrocarbon groups which, in the context of this invention, do not alter the predominantly hydrocarbyl character of the substituent. Those skilled in the art will be aware of suitable groups (e.g., halo, especially chloro and fluoro, amino, alkoxyl, mercapto, alkylmercapto, nitro, nitroso, sulfoxy, etc.)
3. Hetero substituents, that is, substituents which, while predominantly hydrocarbon in character within the context of this invention, contain atoms other than carbon present in a chain or ring otherwise composed of carbon atoms.

Importantly, the organo groups of the ligands have a sufficient number of carbon atoms to render the compound soluble or dispersible in the oil. For example, the number of carbon atoms in each group will generally range between about 1 to about 100, preferably from about 1 to about 30, and more preferably between about 4 to about 20. Preferred ligands include dialkyldithiophosphate, alkylxanthate, and dialkyldithiocarbamate, and of these dialkyldithiocarbamate is more preferred. Organic ligands containing two or more of the above functionalities are also capable of serving as ligands and binding to one or more of the cores. Those skilled in the art will realize that formation of the compounds of the present invention requires selection of ligands having the appropriate charge to balance the core's charge.

Compounds having the formula $Mo_3S_kL_nQ_z$ to have cationic cores surrounded by anionic ligands and are represented by structures such as

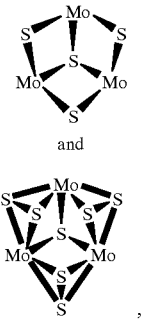

and and have net charges of +4. Consequently, in order to solubilize these cores the total charge among all the ligands must be −4. Four monoanionic ligands are preferred. Without wishing to be bound by any theory, it is believed that two or more trinuclear cores may be bound or interconnected by means of one or more ligands and the ligands may be multidentate. Such structures fall within the scope of this invention. This includes the case of a multidentate ligand having multiple connections to a single core. It is believed that oxygen and/or selenium may be substituted for sulfur in the core(s).

Oil-solule or dispersible trinuclear molydenum compounds can be prepared by reacting in the appropriate liquid(s)/solvent(s) a molybdenum source such as $(NH_4)_2Mo_3S_{13} \cdot n(H_2O)$, where n varies between 0 and 2 and includes non-stoichiometric values, with a suitable ligand source such as a tetralkylthiuram disulfide. Other oil-soluble or dispersible trinuclear molybdenum compounds can be formed during a reaction in the appropriate solvent(s) of a molybdenum source such as of $(NH_4)_2Mo_3S_{13} \cdot n(H_2O)$, a ligand source such as tetralkylthiuram disulfide, dialkyldithiocarbamate, or dialkyldithiophosphate, and a sulfur abstracting agent such cyanide ions, sulfite ions, or substituted phosphines. Alternatively, a trinuclear molybdenum-sulfur halide salt such as $[M']_2[Mo_3S_7A_6]$, where M' is a counter ion, and A is a halogen such as Cl, Br, or I, may be reacted with a ligand source such as a dialkyldithiocarbamate or dialkyldithiophosphate in the appropriate liquid(s)/solvent(s) to form an oil-soluble or dispersible trinuclear molybdenum compound. The appropriate liquid/solvent may be for example aqueous or organic.

In general, the compounds prepared as outlined above can be purified by well known techniques such as chromatography and the like; however, it may not be necessary to purify the compounds. Crude mixtures that contain substantial amounts of the compound have been found to be effective.

A compound's oil solubility or dispersibility may be influenced by the number of carbon atoms in the ligands' organo groups. In the compounds of the present invention, at least 21 total carbon atoms should be present among all the ligands' organo groups. Preferably, the ligand source chosen has a sufficient number of carbon atoms in its organo groups to render the compound soluble or dispersible in the lubricating composition.

The terms "oil-soluble" or "dispersible" used herein do not necessarily indicate that the compounds or additives are soluble, dissolvable, miscible, or capable of being suspended in the oil in all proportions. These do mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive, if desired.

The lubricating compositions of the present invention may contain a minor effective amount, preferably about 1 ppm to 2,000 ppm molybdenum from the trinuclear molybdenum compound, more preferably from 5 to 750 ppm, and most preferable from 10 to 300 ppm, all based on the weight of the lubricating composition.

Concentrates of the compounds of the present invention in a suitable oleagenous carrier provide a convenient means of handling the compounds before their use. Oils of lubricating viscosity, such as those described above, as well as aliphatic, naphthenic, and aromatic hydrocarbons are examples of suitable carriers for concentrates. These concentrates may contain about 1 to about 90 weight percent of the compound based on the weight of the concentrate, preferably from about 1 to about 70 weight percent, and more preferably from about 20 to about 70 weight percent.

Other known lubricant additives may be compatible with the invention and can be used for blending in the lubricant composition of this invention. These include for example friction-reducing agents, dispersants, single or mixed metal detergents, pour point depressants, viscosity improvers, antioxidants, surfactants, and antiwear agents. These can be combined in proportions known in the art. For example, beneficial lubricant additives containing phosphorous and/or sulfur compounds such as ZDDP may be prepared and used with the compounds of the present invention. However, the compounds of the present invention may be effective or may even possess improved properties when used in lubricating compositions that are free or substantially free of phosphorus and/or sulfur except for the phosphorus or sulfur contained in the trinuclear molybdenum compounds of the present invention. A lubricating composition that is substantially free of phosphorous and/or sulfur is one in which the amount of phosphorus and/or sulfur is less than is inherently present in oils of lubricating viscosity.

The trinuclear molybdenum compounds of the present invention also possess antioxidant properties when used in a lubricating composition. Tests using the model compound cumene hydroperoxide in mineral oil basestock revealed that compounds having $Mo_3S_k$ cores are more effective antioxidants than either conventional organic antioxidants or commercially available dinuclear molybdenum additive compounds such as dinuclear molybdenum alkylated dithiocarbamate.

The lubricating compositions and concentrates of this invention comprise defined components that may or may not remain the same chemically before and after mixing with an oleagenous carrier. This invention encompasses compositions and concentrates which comprise the defined components before mixing, or after mixing, or both before and after mixing.

The invention will be more fully understood by reference to the following examples illustrating various modifications of the invention which should not be construed as limiting the scope thereof As used herein, ddp represents dialkyldithiophosphate, dtc represents dialkyldithiocarbamate, and coco represents an alkyl chain or mixture of chains of varying even numbers of carbon atoms from about typically $C_8$ to $C_{18}$.

EXAMPLE 1
Synthesis of $Mo_3S_4[(2\text{-ethylhexyl})_2dtc]_4$ by Abstraction of Sulfur with Sulfite in Water $(NH_4)_2Mo_3S_{13}\cdot 2H_2O$ (0.77 g, 1 mmol) was added to a solution of potassium bis(2-ethylhexyl)dithiocarbamate (2.13 g, 6 mmol) in water (50 mL). In another flask, potassium sulfite (0.95 g, 6 mmol) was dissolved in water (50 mL). The solution of potassium sulfite was added dropwise to the molybdenum/dialkyldithiocarbamate mixture. The mixture was allowed to react for 24 hours at room temperature. The product was extracted with ether and then the ether solution was filtered. The ether was pumped off, the product extracted with methanol (3×30 mL), and the product was dried under vacuum to yield $Mo_3S_4[(2\text{-ethylhexyl})_2 dtc]_4$.

EXAMPLE 2
Synthesis of $Mo_3S_4[(2\text{-ethylhexyl})_2dtc]_4$. by Abstraction of Sulfur with Cyanide in Water $(NH_4)_2Mo_3S_{13}\cdot 2H_2O$ (0.77 g, 1 mmol) was added to a solution of potassium bis(2-ethylhexyl)dithiocarbamate (2.13 g, 6 mmol) in water (50 mL). In another flask, potassium cyanide (0.39 g, 6 mmol) was dissolved in water (50 mL). The solution of potassium cyanide was added dropwise to the molybdenum/dialkyldithiocarbamate mixture. The mixture was allowed to react for 24 hours at room temperature. The product was extracted with ether and then the ether solution was filtered. The ether was pumped off, the resulting product extracted with methanol (3×30 mL), and the product was dried under vacuum to yield $Mo_3S_4[(2\text{-ethylhexyl})_2dtc]_4$.

EXAMPLE 3
Synthesis of $Mo_3S_4[(2\text{-ethylhexyl})_2ddp]_4$. by Abstraction of Sulfur with Phosphine An acetonitrile (50 mL) solution containing $(NH_4)_2 Mo_3S_{13}\cdot 2H_2O$ (0.77 g, 1.0 mmol) and $PPh_3$ (1.57 g, 6.0 mmol) and bis(2-ethylhexyl)dithiophosphoric acid (2.34 g, 6.6 mmol) was refluxed for 24 hours and then cooled to room temperature. The acetonitile was decanted off and the product was washed 2× with methanol (20 mL). The product was dissolved in pentane and filtered; the pentane was evaporated to a minimum and the solution filtered again followed by removal of pentane to yield $Mo_3S_4[(2\text{-ethylhexyl})_2ddp]_4$.

EXAMPLE 4
Synthesis of $Mo_3S_4[(octyl)_2dtc_2]_4$ by Abstraction of Sulfur with Cyanide using Thiuram Disulfide as Ligand Source A methanol (50 mL) solution containing $(NH_4)_2 Mo_3S_{13}\cdot 2H_2O$ (0.77 g, 1.0 mmol) and KCN (0.585 g, 9.0 mmol) and tetraoctyl thiuram disulfide (2.1 g, 3.3 mmol) was refluxed for 24 hours and then cooled to room temperature. The methanol was decanted off and the product was washed 2× with ethanol (20 mL). The product was dissolved in a minimum of pentane and filtered; the pentane was evaporated to yield $Mo_3S_4(octyl_2dtc)_4$.

EXAMPLE 5
Synthesis of $Mo_3S_7[(lauryl)_2ddp]_4$

To a solution of potassium dilauryldithiophosphate (2.2 g, 4.4 mmol) in methanol (100 mL) was added a solution of $[NEt_4]_2[Mo_3S_7Cl_6]$ (0.98 g, 0.1 mmol) in acetonitril (50 mL). The combined solution was heated at 60° C. with stirring for 12 h. The solution was decanted and the product was washed with methanol followed by acetonitrile. The product was dissolved in pentane and filtered. The solvent was pumped off to yield $Mo_3S_7(lauryl_2ddp)_4$.

EXAMPLE 6

Synthesis of $Mo_3S_7[(2\text{-ethylhexyl}_2\text{dtc})_4]$

A 1:1 methanol/THF solution containing $(NH_4)_2Mo_3S_{13}\cdot 2H_2O$ (3.88 g, 5.0 mmol) and tetra(2-ethylhexyl) thiuram disulfide (9.5 g, 15 mmol) was heated at 60° C. for 24 hours and cooled to room temperature. The solution was filtered, the solvent pumped off, and the product washed with methanol. The product was dissolved in THF, the resulting solution filtered, and the solvent pumped off to yield $Mo_3S_7(2\text{-ethylhexyl}_2\text{dtc})_4]$.

The $Mo_3S_kL_4$ (k=4–7) compounds are related by the number of sulfur atoms in the molybdenum-sulfur core. The number of the sulfur atoms in the core may be altered by the addition of sulfur abstractors such as cyanide and substituted phosphines or sulfur donators such as elemental sulfur and organic trisulfides to the $Mo_3S_kL_4$ compounds.

In Examples 7 through 10, the compounds of the invention were evaluated for friction and wear performance using a Falex block-on-ring tribometer. The data was obtained at a speed of 420 rpm, load of 100 kg (220 lb.), and a temperature of 100° C. for 2h. Data reported include block wear scar volume, measured by profilometry, the end of test friction coefficient (Last Coef.), and the (Avg. Coef.) friction coefficient over the 2 hour test. The end of the test friction coefficient is that obtained at the end of the test, and the average friction coefficient provides information, on the activity of the added material, i.e., samples that attain the same decreased friction coefficients faster are considered to contain more active friction reducing compounds. In examples 7–10 the samples tested consisted of Solvent 150 Neutral (S150N) lubricating oil, 1% ZDDP, and compounds of the present invention having 500 ppm molybdenum based on the total weight of the lubricating oil.

The procedures and equipment used in Examples 7 through 10 are similar to those used in ASTM Test G77–83 (Ranking Resistance of Materials to Sliding Wear Using Block-on-Ring Wear Test.

Comparative Example 11

For comparative purposes, the Falex block-on-ring was conducted using only Solvent 150 Neutral (S150N) and 1% ZDDP. The results are shown in Table I.

TABLE I

| Test Run | Compound | Wear ($10^{-2}$ mm$^3$) | Friction Last Coef. | Friction Avg. Coef. |
|---|---|---|---|---|
| Ex. 7 | $Mo_3S_4[(C_8H_{17})_2dtc]_4$ | 1.69 | 0.041 | 0.057 |
| Ex. 8 | $Mo_3S_4[(C_8H_{17})_2ddp]_4$ | 1.64 | 0.040 | 0.060 |
| Ex. 9 | $Mo_3S_7[(C_{13}H_{27})_2dtc]_4$ | 0.80 | 0.063 | 0.078 |
| Ex. 10 | $Mo_3S_7[(C_{13}H_{27})_2ddp]_4$ | 0.74 | 0.059 | 0.064 |
| Ex. 11 | None | 0.91 | 0.113 | 0.115 |

EXAMPLES 12 to 15

In these examples, the compounds of the invention were evaluated for friction and wear performance as described for Examples 7 through 10. In examples 12–15 the samples tested consisted of a 10W30 fully formulated oil combined with compounds of the present invention having 500 ppm molybdenum based on the total weight of the lubricating oil.

Comparative Example 16

For comparative purposes, the Falex block-on-ring was conducted using a 10W30 fully formulated motor oil. The results are shown in Table II.

TABLE II

| Test Run | Compound | Wear ($10^{-2}$ mm$^3$) | Friction Last Coef. | Friction Avg. Coef. |
|---|---|---|---|---|
| Ex. 12 | $Mo_3S_4[(C_8H_{17})_2dtc]_4$ | 0.58 | 0.032 | 0.040 |
| Ex. 13 | $Mo_3S_4[(C_8H_{17})_2ddp]_4$ | 0.58 | 0.029 | 0.038 |
| Ex. 14 | $Mo_3S_7[(C_{13}H_{27})_2dtc]_4$ | 0.71 | 0.032 | 0.044 |
| Ex. 15 | $Mo_3S_7[(C_{13}H_{27})_2ddp]_4$ | 0.62 | 0.035 | 0.044 |
| Ex. 16 | None | 2.86 | 0.132 | 0.130 |

EXAMPLES 17–20

Differential scanning calorimetry (DSC) tests were conducted on samples in Solvent 150 Neutral (S150N) with compounds of the present invention having 500 ppm molybdenum based on the total weight of the lubricating oil. In this DSC test, a sample of the oil is heated at a rate of e.g., 5° C./minute and the rise in sample temperature relative to an inert reference is measured. The temperature at which an exothermic reaction occurs or the oxidation onset temperature is a measure of the oxidative stability of the sample. It is believed that higher DSC temperatures indicate improved oxidative stability compared with compounds having lower DSC temperatures. The results of the tests are shown in Table III.

Comparative Example 21

The DSC test was performed with Solvent 150 Neutral (S150N) for comparative purposes. The results are shown in Table III.

TABLE III

| Test Run | Compound | DSC (° C.) |
|---|---|---|
| Ex. 17 | $Mo_3S_4[(C_8H_{17})_2dtc]_4$ | 285 |
| Ex. 18 | $Mo_3S_4[(C_8H_{17})_2ddp]_4$ | 285 |
| Ex. 19 | $Mo_3S_7[(C_{13}H_{27})_2dtc]_4$ | 268 |
| Ex. 20 | $Mo_3S_7[(C_{13}H_{27})_2ddp]_4$ | 277 |
| Ex. 21 | None | 212 |

EXAMPLE 22

The compounds of this invention were evaluated for their ability to decompose hydroperoxides. Hydroperoxides are known to engage in reactions that degrade the lubricant, consume additives, and cause viscosity increase, wear, and formation of sludge and deposits. In this test a compound in a base stock mixture (2.25:1 mixture of Solvent 150 Neutral (S150N): Solvent 100 Neutral (S100N) by weight) containing ZDDP is reacted with a known amount of cumene hydroperoxide (CHP). The CHP and the compound solution are reacted at a temperature of 125° C. for one hour and the product is analyzed by gas chromatography linked with mass spectrometry (GC/MS). The amount of CHP consumed indicates how effective the compound is at neutralizing hydroperoxides, i.e., a higher amount indicates better antioxidancy. The elemental molybdenum concentration in the test solution was constant.

In compositions A and B the base stock contained a primary ZDDP and a trinuclear molybdenum compound. For comparison, composition C also contained a primary ZDDP and a commercial dinuclear molybdenum lubricant additive, $Mo_2O_2S_2(dtc)_2$ which has a mixture of $octyl_2dtc$ and $coco_2dtc$ ligands. In compositions D and E, the base stock contained a secondary ZDDP and a trinuclear molybdenum compound. For comparison, composition F contained a secondary ZDDP and $Mo_2O_2S_2(dtc)_2$.

TABLE IV

| Composition CHP | Compound | Moles of CHP consumed per mole of compound | Moles of CHP consumed per mole of molybdenum |
|---|---|---|---|
| A | $Mo_3S_4[(2\text{-ethylhexyl})_2dtc]_4$ | 8560 | 2853 |
| B | $Mo_3S_7[(coco)_2dtc]_4$ | 7327 | 2442 |
| C | $Mo_2O_2S_2(dtc)_2$ | 1120 | 560 |
| D | $Mo_3S_4[(2\text{-ethylhexyl})_2dtc]_4$ | 7973 | 2658 |
| E | $Mo_3S_7[(coco)_2dtc]_4$ | 8473 | 2824 |
| F | $Mo_2O_2S_2(dtc)_2$ | 1174 | 587 |

Table IV shows that the trinuclear molybdenum compounds of the present invention decompose CHP approximately seven times better than the commercial dinuclear additive on a molecular basis in this test. On a normalized molybdenum mole basis, the novel trinuclear compounds perform four to five times better than the commercial dinuclear molybdenum additive in this test.

EXAMPLE 23

In this example, compounds of the present invention and a commercial additive were evaluated for friction and wear performance. The samples were run at a concentration of 500 ppm molybdenum in a sulfur-free synthetic basestock with added esters to increase the solubility of the molybdenum compounds in the synthetic lubricating oil.

Table V shows performance results for the trinuclear molybdenum compounds of the present invention versus a commercial molybdenum additive. A comparative example using an oil substantially free of sulfur and containing no added molybdenum compounds was not possible because the oil alone caused seizure during test start-up before the 220 lb. (100 kg) load was reached.

TABLE V

| Compound | Wear ($10^{-2}$ mm$^3$) | Friction Last Coef. | Friction Avg. Coef. |
|---|---|---|---|
| $Mo_3S_7[(coco)_2dtc]_4$ | 2.76 | 0.052 | 0.061 |
| $Mo_2O_2S_2[(coco)_2dtc]_2$ | 2.33 | 0.097 | 0.089 |

The trinuclear molybdenum dithiocarbamate compounds reduces friction in sulfur free basestocks more than the dinuclear molybdenum dithiocarbamate.

EXAMPLE 24

In this example, the compounds of the invention and commercial additives were evaluated for friction and wear performance in a Falex block-on-ring test procedure. The data was acquired at a speed of 420 rpm, load of 220 lb. (100 kg), and a temperature of 100° C. for 120 minutes. The samples were run at a concentration of 500 ppm molybdenum in a fully formulated motor oil without ZDDP (a common antiwear additive) and no additional phosphorus containing compounds. Although some of the molybdenum compounds contain phosphorus, the molybdenum compounds were added at a lower treat rate than is typically used for ZDDP and contain less phosphorus by weight. Total phosphorus concentration in these oils was <0.02%.

Trials 1 through 4 show performance results of samples of trinuclear molybdenum dithiocarbamates of the present invention and commercial dinuclear molybdenum dithiocarbamates; these test cases are phosphorus free. Trials 5 through 7 exhibit the performance of the trinuclear molybdenum compounds of the present invention and a commercial dinuclear additive with dithiophosphate ligands. The samples in trials 5 through 7 are substantially free of phosphorous beyond that contained in the ligands. A lubricating composition that is substantially free of phosphorus is on in which the amount of phosphorus is no more than is inherently present in base oils of lubricating viscosity. For comparison purposes, trial 8 shows the performance of the fully formulated motor oil without ZDDP used as the lubricating oil in the test; this test case was phosphorus free.

TABLE VI

| Trial | Compound | Wear ($10^{-2}$ mm$^3$) | Friction Last Coef. | Friction Avg. Coef. |
|---|---|---|---|---|
| 1 | $Mo_3S_4[(octyl)_2dtc]_4$ | 1.01 | 0.036 | 0.042 |
| 2 | $Mo_3S_7[(coco)_2dtc]_4$ | 0.92 | 0.033 | 0.042 |
| 3 | $Mo_2O_2S_2[(octyl)_2dtc]_2$ | 1.43 | 0.051 | 0.065 |
| 4 | $Mo_2O_2S_2[(coco)_2dtc]_2$ | 1.48 | 0.053 | 0.061 |
| 5 | $Mo_3S_4[(octyl)_2ddp]_4$ | 1.14 | 0.044 | 0.048 |
| 6 | $Mo_3S_7[(lauryl)_2ddp]_4$ | 1.29 | 0.064 | 0.058 |
| 7 | $Mo_2O_2S_2[(octyl)_2ddp]_2$ | 1.81 | 0.060 | 0.065 |
| 8 | None | 1.81 | 0.112 | 0.113 |

The trinuclear molybdenum dithiocarbamate compounds exhibit better wear and friction performance than the commercial additives in formulations without ZDDP.

What is claimed is:

1. A lubricating oil composition comprising a major amount of an oil of lubricating viscosity and a minor amount of at least one trinuclear molybdenum compound sufficient to provide said lubricating oil composition with at least 1 ppm of molybdenum.

2. The lubricating composition of claim 1, wherein the trinuclear molybdenum compound has a sulfur-containing core.

3. The lubricating composition of claim 1, wherein the trinuclear molybdenum compound is selected from compounds having the formula $Mo_3S_kL_nQ_z$, and mixtures thereof, wherein L represents independently selected ligands, n is 1 to 4, k is 4 through 7, Q is an electron donating compound, and z is 0 to 5.

4. The lubricating composition of claim 3 wherein the neutral electron donating compound is selected from the group of water, amines, alcohols, phosphines, and ethers.

5. The lubricating composition of claim 3 wherein the ligands, L, are represented by one or more of the structures having the formula

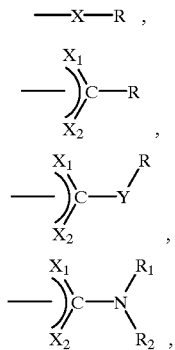

-continued

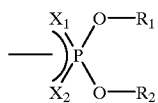

wherein X, $X_1$, $X_2$, and Y are oxygen or sulfur and wherein $R_1$, $R_2$, and R are independently selected from the group of hydrogen and organo groups.

6. The lubricating composition of claim 5 wherein the organo groups are independently selected from alkyl, aryl, substituted aryl, and ether groups.

7. The lubricating composition of claim 6 wherein the organo groups are alkyl groups and the number of carbon atoms in each alkyl group ranges from about 1 to 100.

8. The lubricating composition of claim 7 wherein the number of carbon atoms in each alkyl group ranges from about 4 to about 20.

9. The lubricating composition of claim 8 wherein the ligands are independently selected from the group of dialkyldithiophosphate, thioxanthates, dialkylphosphate, dialkyldithiocarbamate, dialkylthiophosphate, and xanthates.

10. The composition of claim 5 wherein the trinuclear molybdenum compound ligand's organo groups have a sufficient number of carbon atoms to render the trinuclear molybdenum compound soluble or dispersible in oil.

11. The lubricating composition of claim 5 wherein the trinuclear molybdenum compounds have a total of at least 21 carbon atoms among all the ligands' organo groups.

12. The lubricating composition of claim 1 wherein the weight of the molybdenum from the trinuclear molybdenum compound ranges from 1 to 1000 ppm based on the weight of the lubricating composition.

13. The lubricating composition of claim 1 wherein the molybdenum in the trinuclear molybdenum compound is in the +4 oxidation state.

14. The composition of claim 1 wherein the trinuclear molybdenum compound is oil soluble.

15. The composition of claim 1 wherein the trinuclear molybdenum compound is dispersible in oil.

16. The lubricating composition of claim 2 wherein the trinuclear molybdenum compound contains sulfur and wherein the lubricating composition further comprises added sulfur containing compounds.

17. The lubricating composition of claim 1 wherein the trinuclear molybdenum compound contains sulfur and wherein the lubricating composition is substantially free of added sulfur containing compounds.

18. The lubricating composition of claim 1 wherein the trinuclear molybdenum compound contains phosphorus and wherein the lubricating composition further comprises added phosphorus containing compounds.

19. The lubricating composition of claim 1 wherein the trinuclear molybdenum compound contains phosphorus and wherein the lubricating composition is substantially free of added phosphorus containing compounds.

20. The lubricating composition of claim 1 wherein the oil is substantially free of sulfur.

21. An additive concentrate for blending with lubricating oils comprising an oleagenous carrier and from about 1 to about 200,000 ppm by weight of the molybdenum of a trinuclear molybdenum compound based on the weight of the concentrate.

22. A method for preparing an oil soluble trinuclear thiomolybdenum compound comprising combining a liquid containing a molybdenum source, a ligand source, and a sulfur source other than the molybdenum source in order to form an oil soluble trinuclear thiomolybdenum compound.

23. The method of claim 22 wherein the molybdenum source is selected from the group of $Mo_3S_{13}^{2-}$ and trinuclear thiomolybdenum halides.

24. The method of claim 22 wherein the liquid is water.

25. The method of claim 22 wherein the liquid is an organic liquid.

26. The product of claim 22.

27. A method for preparing a lubricating oil composition comprising combining an oil of lubricating viscosity and an amount of a trinuclear molybdenum compound sufficient to provide said lubricating oil composition with at least about 1 ppm of molybdenum.

28. The product of claim 27.

29. A compound having the formula $Mo_3S_kL_nQ_z$ wherein the L are independently selected ligands, n varies from 1 to 4, k varies from 4 through 7, Q is selected from the group of neutral electron donating compounds, and z ranges from 0 to 5, wherein the compound has a core selected from the group of cores having the structures

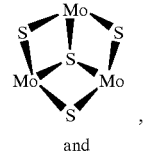

and

and ligands selected from the group of ligands having the formulas

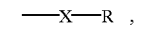

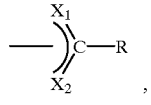

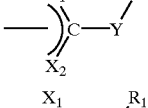

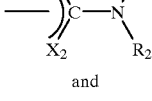

and

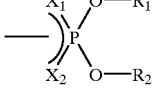

wherein X, $X_1$, $X_2$, and Y oxygen or sulfur and wherein $R_1$, $R_2$, and R are independently selected the group of hydrogen and organo groups, wherein at least 21 carbon atoms are present among all the ligands' organo groups.

30. A lubricating composition comprising a major amount of an oil of lubricating viscosity and a minor amount of a compound having the formula $Mo_3S_kL_nQ_z$ wherein the L are independently selected ligands, n varies from 1 to 4, k varies from 4 through 7, Q is selected from the group of neutral electron donating compounds, and z ranges from 0 to 5, wherein the compound has a core selected from the group of cores having the structures

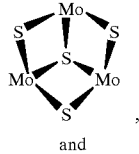

and

and ligands selected from the group of ligands having the formulas

—X—R ,

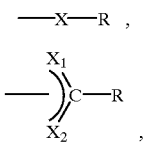

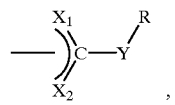

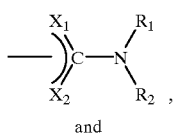

and

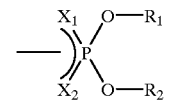

wherein X, $X_1$, $X_2$, and Y oxygen or sulfur and wherein $R_1$, $R_2$, and R are independently selected the group of hydrogen and organo groups.

31. A method for lubricating an internal combustion engine, comprising: adding to an oil of lubricating viscosity a compound containing at least one trinuclear molybdenum core in an amount sufficient to provide said oil with at least 1 ppm of molybdenum, and treating moving parts of the internal combustion engine with said oil.

* * * * *